US00PP12793P2

(12) United States Plant Patent
Ceciliano

(10) Patent No.: US PP12,793 P2
(45) Date of Patent: Jul. 23, 2002

(54) DRACAENA PLANT NAMED 'LIMELIGHT'

(75) Inventor: Julio Gamboa Ceciliano, San Jose (CR)

(73) Assignee: Florica Farms, Inc., Wellingham, FL (US)

( * ) Notice: Subject to any disclaimer, the term of this patent is extended or adjusted under 35 U.S.C. 154(b) by 0 days.

(21) Appl. No.: 09/532,732

(22) Filed: Mar. 22, 2000

(51) Int. Cl.[7] ..... A01H 5/00

(52) U.S. Cl. ..... Plt./383

(58) Field of Search ..... Plt./383

*Primary Examiner*—Bruce R. Campell
*Assistant Examiner*—W C Baker
(74) *Attorney, Agent, or Firm*—Foley & Lardner

(57) ABSTRACT

A new and distinct cultivar of Dracaena plant named 'Limelight', characterized by having bright, glossy yellow-green foliage which darkens to light-green as it matures; slow growth rate; and long-lasting lime/green color retention in low foot-candle situations.

1 Drawing Sheet

BACKGROUND OF THE INVENTION

The present invention comprises a new and distinct cultivar of Dracaena plant, botanically known as *Dracaena deremensis,* and hereinafter referred to by the cultivar name 'Limelight'. The genus Dracaena is a member of the family Liliaceae.

Dracaena is a monocotyledonous tropical foliage plant which can be produced as a single or multi-stemmed plant for interior use or outdoors in shade in zones 9 or 10 only.

The new cultivar was selected by the inventor, Julio Gamboa Ceciliano, in Costa Rica on May 1, 1988. The cultivar was discovered as a naturally-occurring, branch mutation of *Dracaena deremensis* 'Warneckii' (unpatented).

'Limelight' is characterized by producing an inconspicuous raceme inflorescence once annually in optimum growing conditions. The flower is borne at the apical meristem and emerges from the leaf whorl at the top of the plant. Roots of 'Limelight' are fibrous and aromatic with a distinct light orange color.

The new cultivar was first asexually propagated in Costa Rica on Jun. 1, 1988 by Julio Gamboa Ceciliano. Subsequent asexual reproduction of the new cultivar by tissue culture has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and in combination distinguish 'Limelight' as a new and distinct cultivar:

1. Bright, glossy, yellow-green foliage which darkens to light-green as it matures;
2. Slow growth rate;
3. Long-lasting lime/green color retention in low foot-candle situations.

'Limelight' was grown in tropical lowlands in Costa Rica with day lengths of 12 to 13 hours and ambient temperatures of 65 to 85 degrees Fahrenheit. The light levels in lux were 30 K and the level of relative humidity was 80%.

Of the many commercial cultivars known to the present inventor, the most similar in comparison to 'Limelight' is the cultivar 'Janet Craig' (unpatented). In comparison to 'Janet Craig', 'Limelight' is similar in form and habit, but its foliage is bright, yellow-green in color which darkens to light-green as it matures. 'Limelight' also has a slower growth rate than 'Janet Craig'.

BRIEF DESCRIPTION OF THE DRAWING

The accompanying photographic illustration shows the distinctive yellow/green color of the foliage of a typical 'Limelight' plant following growth under appropriate growing conditions, with colors being as true as possible with illustrations of this type.

DETAILED BOTANICAL DESCRIPTION

The following observations, measurements and values describe approximately 3 to 4 year old plants grown under greenhouse conditions which closely approximate those generally used in horticultural practice. Color references are made to The Royal Horticultural Society Colour Chart (R.H.S.), except where general colors of ordinary significance are used.

Classification:
*Botanical.*—*Dracaena deremensis.*
Parentage: Naturally-occurring mutation of *Dracaena deremensis* 'Warneckii'.
Propagation: Vegetative, by airlayer or rooted cuttings.
Plant habit:
*Growth rate.*—Approximately 30 inches annually.
*Form.*—Monocot; leaves whorled; leaf bases wrap around the stem.
*Plant height.*—Maximum of 15 feet when grown in the ground and 6 feet when grown in a container.
*Plant width.*—Single stem plant has an overall plant diameter of 22–30 inches wide.
Foliage:
*Form and size.*—Overall leaf shape is lanceolate, lightly pendulous; base obtuse, acute apex; approximately 14–18 inches long and 2½–4 inches wide.
*Texture.*—Longitudinally ribbed lustrous.
*Veins.*—Parallel with distinct midrib.

*Color*.—New growth bright yellow/green, older foliage darkens to light green.

*Mature leaf*.—Upper Surface: Yellow-green RHS 144A. Lower Surface: Yellow-green, RHS 144A.

*Newly expanded leaf*.—Upper Surface: Greener than but closest to yellow-green, RHS 151D. Lower Surface: Greener than but closest to yellow-green, RHS 151D.

*Margin*.—Entire, slightly undulate, acuminate leaf rolled ¼ inch at apex.

*Thickness*.—Less than $1/64^{th}$ inches thick.

Stem:

*Length*.—Up to 6 feet when grown in a container.

*Thickness*.—Cylindrical, ½ to 1½ inches thick.

*Color*.—Light to medium-green, greener than but closest to RHS 151 D.

Roots: Mostly fibrous; light-orange in color; aromatic.

Resistance to pests and disease: Typical, no special observations made.

I claim:

1. A new and distinct cultivar of Dracaena plant named 'Limelight', as described and illustrated.

* * * * *

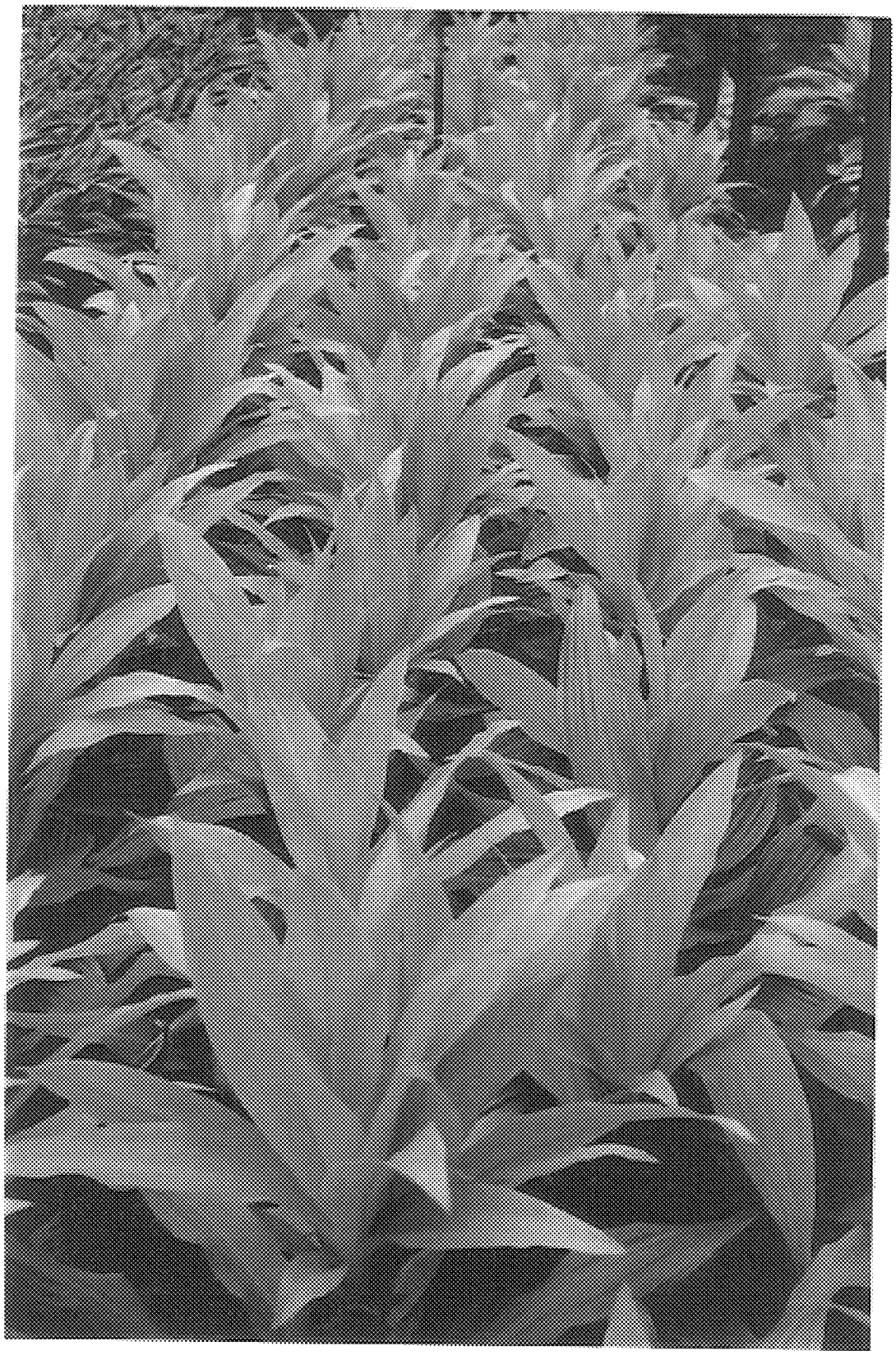

UNITED STATES PATENT AND TRADEMARK OFFICE

CERTIFICATE OF CORRECTION

PATENT NO. : PP 12,793 P2
DATED : July 23, 2002
INVENTOR(S) : Julio Gamboa Ceciliano It is certified that error appears in the above-identified patent and that said Letters Patent is hereby corrected as shown below:

Title page,
Item [73], Assignee, please delete "Wellingham" and insert instead -- Wellington --.

Signed and Sealed this

Thirty-first Day of December, 2002

JAMES E. ROGAN
*Director of the United States Patent and Trademark Office*